(12) United States Patent
Jacob

(10) Patent No.: US 9,133,328 B2
(45) Date of Patent: Sep. 15, 2015

(54) PLASTIC COMPOSITIONS AND CONTAINERS MADE THEREOF

(75) Inventor: Anne-Flore Jacob, Sciez (FR)

(73) Assignee: SA DES EAUX MINERALES D'EVIAN SAEME, Evian-les-Bains (FR)

(*) Notice: Subject to any disclaimer, the term of this patent is extended or adjusted under 35 U.S.C. 154(b) by 0 days.

(21) Appl. No.: 14/364,314

(22) PCT Filed: Dec. 12, 2011

(86) PCT No.: PCT/IB2011/003254
§ 371 (c)(1),
(2), (4) Date: Jul. 16, 2014

(87) PCT Pub. No.: WO2013/088192
PCT Pub. Date: Jun. 20, 2013

(65) Prior Publication Data
US 2014/0371355 A1    Dec. 18, 2014

(51) Int. Cl.
| | |
|---|---|
| C08L 25/06 | (2006.01) |
| C08J 5/18 | (2006.01) |
| B29C 47/00 | (2006.01) |
| C08L 51/04 | (2006.01) |
| B32B 27/30 | (2006.01) |
| B29K 25/00 | (2006.01) |
| B29K 35/00 | (2006.01) |
| B29K 201/00 | (2006.01) |
| B29L 31/00 | (2006.01) |

(52) U.S. Cl.
CPC ............ C08L 25/06 (2013.01); B29C 47/0004 (2013.01); B29C 47/0054 (2013.01); B32B 27/302 (2013.01); C08J 5/18 (2013.01); C08L 51/04 (2013.01); B29K 2025/06 (2013.01); B29K 2035/00 (2013.01); B29K 2201/00 (2013.01); B29L 2031/712 (2013.01); B32B 2262/06 (2013.01); B32B 2270/00 (2013.01); B32B 2439/70 (2013.01); C08J 2325/06 (2013.01); C08J 2401/00 (2013.01); C08J 2401/02 (2013.01); C08J 2425/06 (2013.01); C08J 2425/08 (2013.01); C08J 2447/00 (2013.01); C08L 2203/30 (2013.01); C08L 2205/02 (2013.01); C08L 2205/025 (2013.01); C08L 2205/03 (2013.01); C08L 2205/035 (2013.01); C08L 2205/16 (2013.01)

(58) Field of Classification Search
USPC ........................................... 524/35; 264/209.3
See application file for complete search history.

(56) References Cited

U.S. PATENT DOCUMENTS 5,474,722 A * 12/1995 Woodhams ................... 264/45.3

FOREIGN PATENT DOCUMENTS

| CN | 10-1875746 A | * 11/2010 | ............... C08K 3/02 |
| CN | 101875746 | * 11/2010 | ............... C08K 3/02 |
| CN | 101875746 A | 11/2010 | |

OTHER PUBLICATIONS

Database WPI, Week 201117, Thomson Scientific, AN 2010-Q00145, 2010, XP002681459.
Antich et al., "Mechanical behavior of high impact polystyrene reinforced with short sisal fibers", Composites: Part A, vol. 37, 2006, pp. 139-150, XP028012880.
Pracella et al., "Thermal and microstructural characterization of compatibilized polystyrene/natural fillers composites", J. Therm. Anal. Calorim., 2011, vol. 103, pp. 95-101, XP19879787.
International Search Report, dated Aug. 16, 2012, from corresponding PCT application.

* cited by examiner

*Primary Examiner* — Robert Harlan
(74) *Attorney, Agent, or Firm* — Young & Thompson

(57) ABSTRACT

A composition includes: a) polystyrene, the polystyrene including polybutadiene; b) vegetal fibers having a length lower than 50 μm; and c) at least one compatibility agent including a polybutadiene maleic anhydride copolymer, the copolymer including at least 17% by weight of the copolymer of maleic anhydride. The composition is used for manufacturing a plastic composition. The plastic composition obtained by heating the composition, a sheet obtained by extruding the plastic composition, and a container obtained by thermoforming the sheet are also described.

16 Claims, 2 Drawing Sheets

PLASTIC COMPOSITIONS AND CONTAINERS MADE THEREOF

BACKGROUND OF THE INVENTION

1. Field of the Invention

The invention concerns polystyrene-based compositions comprising vegetal fibers.

2. Description of the Related Art

Plastic-based compositions are useful for the storage of various products. Today, consumers are sensitive to the use of plastic substitutes, which would come from a vegetal source and be ecologic or perceived as ecologic. Among the currently available plastic substitutes, the vegetal materials for manufacturing alimentary containers often come from genetically modified plants, and are usually in competition with the alimentary content. Moreover, it would be useful to recycle agricultural waste. Said vegetal materials however do not have to be in competition with the alimentary content.

However, vegetal materials do not always fulfill technical requirements, such as the resistance to stretching and/or heating steps (typically performed upon thermoforming) or the resistance to mechanical constraints. When vegetal materials are used for manufacturing containers, like alimentary containers, said containers have to maintain their integrity during processing of the product and storage.

Vegetal materials are also useful because they may replace, at least in part, the use of plastics from oil base.

There is thus a need for a composition comprising vegetal materials and plastics, said composition allowing the manufacture of derived products being resistant to stretching and to vertical compression.

SUMMARY OF THE INVENTION

The invention addresses at least one of the problems or needs above: indeed, the inventors elaborated a composition comprising vegetal fibers, which allows the formation of derived products, like films, sheets or containers, said derived products being resistant to stretching and to vertical compression. Said derived products show good deformability during manufacture, and good resistance to stretching and to vertical compression when finished.

The present invention relates to a specific composition as mentioned below. The composition can be in the form of a plastic composition, typically obtained upon heating so that all ingredients are melted together. The plastic composition can in the form of a sheet or a film, typically obtained by extrusion. The plastic composition can also be in the form of a final product, like a container, typically obtained by submitting a sheet of film to thermoforming.

The present invention thus relates to a composition comprising:
 a) polystyrene, said polystyrene comprising polybutadiene;
 b) vegetal fibers having a length lower than 50 µm; and
 c) at least one compatibility agent comprising a polybutadiene maleic anhydride copolymer, said copolymer comprising at least 17% by weight of the copolymer of maleic anhydride.

Said composition can be in the form of a plastic composition or can be used for manufacturing a plastic composition, typically by a step of heating the mixture of ingredients a), b) and c). Thus, the invention also relates to a plastic composition, typically obtainable by heating said composition.

The invention also relates to a sheet or film, typically obtainable by extruding said plastic composition.

Finally, the present invention relates to a container, typically obtainable by thermoforming said sheet.

DETAILED DESCRIPTION OF THE INVENTION

The initial composition of the invention, also called "composition" in the description, comprises:
 a) polystyrene, said polystyrene comprising polybutadiene;
 b) vegetal fibers having a length lower than 50 µm; and
 c) at least one compatibility agent comprising a polybutadiene maleic anhydride copolymer, said copolymer comprising at least 17% by weight of the copolymer of maleic anhydride.

It is mentioned that in the composition, ingredients a), b) and c) are typically in the form of mixture. Thus the composition can be prepared by mixing ingredients a), b) and c).

Preferably, said polystyrene a) is chosen from High Impact PolyStyrene (HIPS), and mixtures of High Impact PolyStryrene (HIPS) and General Purpose PolyStyrene (GPPS). PolyStyrene, HIPS and GPPS are known by the one skilled in the art, and are commercialized under such references. HIPS is a polymer formulation which comprises a polystyrene matrix in which polybutadiene noduls are included. GPPS comprises polystyrene, but no polybutadiene.

Preferably, said polystyrene a) is a mixture of High Impact PolyStyrene and General Purpose PolyStyrene, in a weight ratio of 30:70 to 60:40, preferably of 50:50.

HIPS may be commercialized under the tradenames Edistir R850, Styron 1200, Total 6541 or Empera 524N. GPPS may be commercialized under the tradenames Styron 678, Edistir 1840, Empera 124N, Total 1340 or 1540.

By "fibers", it is meant elongated pieces having a length and a width. According to the invention, said fibers are of vegetal origin, and have a length lower than 50 µm. In one embodiment all the average length is lower than 50 µm. In one embodiment at least 90% by number or by weight of the fibers have a length lower than 50 µm. Said vegetal fibers b) are preferably chosen from cellulose fibers, flax fibers, hemp fibers, cotton fibers, jute fibers, ramie fibers, sisal fibers, algae fibers and their mixtures.

Preferably, said vegetal fibers b) are present in an amount of 1% to 30% by weight of the total weight of the composition, preferably in an amount of 5% to 20% by weight, preferably 7% to 15% by weight.

Preferably, said fibers are cellulose fibers or hemp fibers having a length lower than 50 µm. Said fibers may be commercialized under the tradenames Arbocel FD600/30 or Vivapur 101 from Rettenmaier.

The composition according to the invention also comprises a compatibility agent c). Said compatibility agent c) comprises a polybutadiene maleic anhydride copolymer, said copolymer comprising at least 17% by weight of the copolymer of maleic anhydride. Without being bound by any theory, it is possible that the polybutadiene maleic anhydride copolymer allows the formation of links with the fibers thanks to the maleic anhydride monomer, and allows links with the polystyrene thanks to the polybutadiene monomer. Said copolymer comprises maleic anhydride in an amount of at least 17% by weight of the copolymer, preferably at least 20% by weight of the copolymer, preferably at least 22% by weight of the copolymer. Preferably, said polybutadiene maleic anhydride copolymer comprises at most 30% by weight of the copolymer of polybutadiene. Preferably, said copolymer is sold under the tradenames Ricobond 1756 or Ricon 131 MA5 by Cray Valley. Said copolymer may also be a butadiene-styrene copolymer adducted with maleic anhydride. In that case, said copolymer may be sold under the tradename Ricon 184MA6 by Cray Valley.

Preferably, the polybutadiene maleic anhydride copolymer is chosen from:
- polybutadiene maleic anhydride copolymers comprising at least 17% by weight of the copolymer of maleic anhydride, and
- mixtures of polybutadiene maleic anhydride copolymers comprising at least 17% by weight of the copolymer of maleic anhydride, and styrene maleic anhydride copolymers.

When present, styrene maleic anhydride copolymers preferably have a maleic anhydride content of 25% and are sold by Cray Valley under the tradenames SMA PRO20783 or SMA PRO20784.

Preferably, said compatibility agent c) is present in an amount of 0.1 to 3% by weight of the total weight of the composition, preferably in an amount of 1 to 1.5% by weight.

The composition according to the invention comprises polystyrene a), vegetal fibers b) and a polybutadiene maleic anhydride copolymer c), said copolymer comprising at least 17% by weight of the copolymer of maleic anhydride.

The composition can be prepared by any appropriate process. Such a process typically involves mixing ingredients a), b) and c). It is mentioned that the process can involve some pre-mixing steps involving at least two of the ingredients of parts thereof. Such mixing and pre-mixing steps are known by the one skilled in the art. One can for example use masterbatch pre-mixes. One can for example mix and heat, typically with an extruder, like a corotary compounding extruder, preferably at a temperature of 180° C. to 200° C., so as to obtain a plastic composition. Preferably, the mixture of ingredients a), b) and c) is performed under heating, so that a homogenous mixture is obtained.

The composition, preferably the plastic composition, can be in the form of powder, granules or pellets.

In one embodiment the composition, typically the (plastic) composition, is in the form of a sheet or a film. These can be obtained by extruding the plastic composition. Extrusion may be performed thanks to a coextruder, like a co extrusion line for 2 layers: one may use said line by feeding a feedblock, which is followed by sheet die and calenders. During extrusion, temperature preferably does not exceed 200° C.

After extrusion, a sheet or film is typically obtained. Said sheet or film has typically a thickness from 0.1 to 5 mm, preferably of from 0.5 to 1.5 mm, for example 0.5 mm, or 0.7 mm, or 0.8 mm, or 0.9 mm, or 1 mm. It is mentioned that the sheet or film can be a monolayer sheet of film, or a multi-layer sheet or film, for example a bi-layer or trilayer sheet or film. In the monolayer case the sheet or film is formed of the composition. In the multi-layer case at least one of the layers, preferably only one, is formed of the composition. Other layers can be formed of different polystyrene compositions, typically without fibers, optionally in a foamed form.

Preferably, in an embodiment, the container has at least a first and a second layers, wherein:
- the first layer results from thermoforming of the sheet according to the invention, and
- the second layer comprises polystyrene, preferably a mixture of High Impact PolyStryrene (HIPS) and General Purpose PolyStyrene (GPPS). Preferably, polystyrene of the second layer is a mixture of High Impact PolyStyrene and General Purpose PolyStyrene, in a weight ratio of 30:70 to 60:40, preferably of 50:50. The second layer may also comprise a colorant.

In said embodiment, said first and second layers are simultaneously produced by extrusion, so that both layers are produced in a bilayer.

The second layer will preferably be used for the internal part of a yogurt container.

In one embodiment the composition, typically the plastic composition, typically the sheet or film can be in the form of a container, typically is a thermoformed form. One can thermoform the sheet so as to obtain the final product of the desired shape. It is mentioned that some stretching occurs upon thermoforming. Thermoforming may be for example performed thanks to a Form Fill Seal thermoforming line. The thermoforming can present the following steps:
- sheet introduction on guide chains (i.e. spike or jaws);
- sheet heating, by heating contact plates;
- forming thanks to a negative mould, assisted by forming plugs and air pressure. The mould may comprise or not a label.

In a Form Fill Seal thermoforming line, one typically performs the following steps after the thermoforming:
- the resulting forms are filled with a product, and then, thermosealed with a lid film,
- finally, they are cutted and optionally precutted by mechanical trimming tool.

Preferably, the sheet is thermoformed so as to obtain a container. Said container may be useful as a dairy product container, like a yogurt container. The invention also concerns the container filled with a food product, preferably a dairy product, preferably or milk-based (milk being an animal milk or a vegetal milk substitute such as soy milk or rice milk etc. . . . ) product preferably a fermented dairy product, for example a yogurt. The container can have a yogurt cup shape, for example with a square cross section or a square with rounded corners cross section, or round cross section. The container has walls (perpendicular to the cross section) provided with elements such as stickers or banderoles. Elements such as banderoles can contribute to re-enforcing the mechanical resistance of the container. The container can be for example a container of 50 ml (or 50 g), to 1 L (or 1 kg), for example a container of 50 ml (or 50 g) to 80 ml (or 80 g), or 80 ml (or 80 g) to 100 ml (or 100 g), or 100 ml (or 100 g) to 125 ml (or 125 g), or 125 ml (or 125 g) to 150 ml (or 150 g), or 150 ml (or 150 g) to 200 ml (or 200 g), or 250 ml (or 250 g) to 300 ml (or 300 g), or 300 ml (or 300 g) to 500 ml (or 500 g), or 500 ml (or 500 g) to 750 ml (or 750 g), or 750 ml (or 750 g) to 1 L (or 1 kg).

The invention also relates to a process of manufacturing a product of a desired shape, preferably a yogurt container, comprising:
i) mixing and heating the following ingredients, so as to obtain a plastic composition:
  a) polystyrene, said polystyrene comprising polybutadiene;
  b) vegetal fibers having a length lower than 50 μm; and
  c) at least one compatibility agent comprising a polybutadiene maleic anhydride copolymer, said copolymer comprising at least 17% by weight of the copolymer of maleic anhydride,
ii) extruding the plastic composition obtained in step i), so as to obtain a sheet or a film,
iii) thermoforming the sheet or film obtained in step ii).

The ingredients of the process are as those described above.

Further details or advantage to the invention might appear in the following non limitative examples.

EXAMPLES

Example 1

Figure 1:
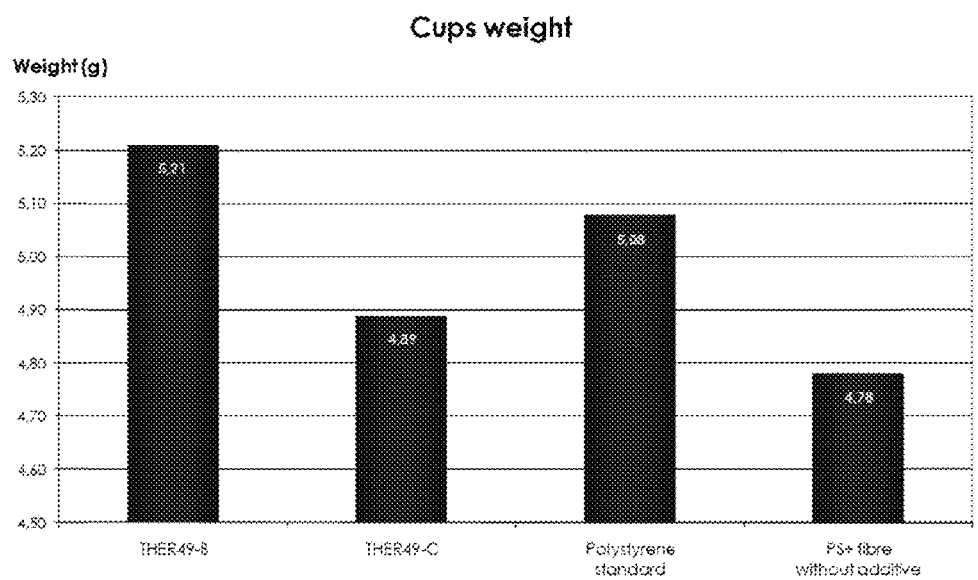
FIG. 1: Cup weights measured in Example 2, following the same protocols as for formulation 1.

Formulations with Different Fibers of Different Lengths

| Formulation 1 | | |
| --- | --- | --- |
| Material (monolayer) | Ratio at extrusion for forming the sheet | % (w/w) in final sheet (formulation 1) |
| HIPS (Edistir R850) | 50% | 50% |
| GPPS (Dow 678) | | 40% |
| Master batch = 80% GPPS (Dow 678) and 20% hemp fibers (250 μm length) | 50% | |
| Hemp fibers (250 μm length) | | 10% |

Sheet of formulation 1 (monolayer) are prepared thanks to the following process:

All the components of the formula are extruded with extruder Fairex with a diameter of 45 mm. Temperature along the screw is comprised between 185 and 195° C., with a speed of 44 rotations per minute. Then compounds aim a die with temperature comprised between 193 and 195° C., and thickness between lips of die is 1 mm. Sheets are then cooled down on 3 calendars that get a temperature of 70° C. and a speed of 0.97 m/min. One obtains 1 mm sheets.

Cups are then prepared with a FFS thermoforming line with following parameters:
- heating plates with a temperature comprised between 155 and 160° C., and six heating steps
- felt forming plugs
- mold cooled down at 15° C.
- forming air pressure at 3 bars
- machine speed 29 strokes per minute.

Observations

The hemp fibers have a high impact on the aspect of the cups: the sheet is dark brown, and the cups are brown.

All cups present micro-holes (with a size of from around 100 μm to 1.3 mm): they are all porous.

The used fibers generate holes in the final product: the polystyrene does not stretch well around fibers. Such micro-holes are detrimental to fool packaging and preservation and for mechanics.

The top load and weight are measured for the cups.

The top load is evaluated according to the following protocol:
- use of a tensile/compression test machine type ADAMEL LHOMARGY DY 34
- apply compression on cups (by 4 cups or by 6 cups) with a speed of 10 mm/min
- evaluate top load value as: maximum of curve, or if curve does not present maximum, take value of force for 3 mm of displacement.
- measurement done on 10 samples.

The cup weights were measured according to the following protocol:
- cup weights: 12 cups per reference were measured by using scale.

The results are as follows:

| | Cup made with sheet of formulation 1 | Cup made with sheet of standard polystyrene (i.e. formulation 1 without hemp fibers) |
| --- | --- | --- |
| Top load (daN) on 6 cups | 24.4 | 42.9 |
| Weight (g) | 4.18 | 4.99 |

The top load is low compared to standard polystyrene, this is believed to be caused by the presence of holes in the cup wall.

| Formulation 2 | | |
| --- | --- | --- |
| Material (monolayer) | Ratio at extrusion for forming the sheet | % (w/w) in final sheet (formulation 1) |
| HIPS (6541) | 0% | 90% |
| GPPS (Dow 678) | | |
| Master batch = 85% HIPS (6541) and 15% cellulose fibers (45 μm length) | 100% | |
| Cellulose fibers (45 μm length) | | 10% |

Sheets and cups are obtained with a similar process as formulation 1.

Observations

With this formulation, there are no more holes, sheets are homogeneous. But they are very brittle.

The top load and weight are also measured on the cups, following the same protocols as for formulation 1.

| | Cup made with sheet of formulation 2 | Cup made with sheet of standard polystyrene (50% HIPS, 50% GPPS) |
| --- | --- | --- |
| Top load (daN) on 4 cups | 8 | 37 |
| Weight (g) | 4.6 | 4.97 |

As a conclusion, the use of fibers with a length lower than 50 μm allows a good homogeneity and avoids the formation of holes in the cups. But it is still not possible to achieve the required top load. It is believed that this is due to the lack of chemical bonding between fibres and polystyrene (PS) (data not shown). Indeed, by different microscopic pictures the inventors can validate that there is no chemical bond between PS and fibers.

Example 2

Formulations with Different Compatibility Agents

Compatibility Agents (or Coupling Agents) Used in the Formulations

- copolymer styrene maleic anhydride (SMA);
- copolymer polybutadiene maleic anhydride (PBuMA);
- copolymer polybutadiene ethylene maleic anhydride (PEMA); or
- copolymer polybutadiene propylene maleic anhydride (PPMA).

Particularly, here are the details about the compatibility agents:

| Supplier | Base | Reference | Molecular weight Mw | Maleic anhydride Rate | Maleic anhydride Position |
|---|---|---|---|---|---|
| Cray Valley | SMA | PRO20784 | | 25% | alternated or random |
| Cray Valley | SMA | PRO20783 | | 25% | alternated or random |
| Cray Valley | PBuMA | Ricobond 1756 | | 17% | grafted 3 maleic anydride by chain |
| Baker Hugues | PEMA | Ceramer 1608 | | 160 acid number | MA graft on PE backbone |
| Baker Huguese | PPMA | X10065 | | | 1 MA on backbone end |
| Polyscope | SMA | XIRAN XZ 09 004 | 180 000 g/mol | 8% | copolymer random |
| Polyscope | SMA | XIRAN XZ 09 002 | 130 000 g/mol | 15% | copolymer random |

To evaluate if the compatibility agent allowed improving cup mechanical properties, said agent is added at fiber compounding before extrusion sheet.

Formulations

The following formulations are prepared:

all sheets are produced as multilayer (a 0.2 mm layer of pure PS for an internal cup part and a 0.8 mm layer of PS+fibers+compatibility agent for an external cup part)

sheets are produced with Scamex diameter 30 mm for internal layer and Fairex diameter 45 mm for layer containing fibers Extrusion temperature is between 185 and 195° C., screw speed is of 39 rpm, feedblock and die are adjusted between 190 and 195° C., calendars temperature is around 70° C. with a speed of 0.86 m/min Thermoforming temperature is between 145 and 150° C., mould is at 15° C. using felt plugs, and machine speed is 29 strokes/min.

| | | Thickness | HIPS Edistir 850E | GPPS Styron 678 | White master batch | HIPS Total 6541 | Compound (15% fiber + 80% total HIPS + 5% coupling agent) | Coupling agent | Fibers (cellulose) |
|---|---|---|---|---|---|---|---|---|---|
| THER 49-A | Internal layer | 0.2 mm | 73% | 25% | 2% | | | | |
| | External layer | 0.8 mm | | | | | SMA PRO20784 100% | | |
| | Total | 1 mm | 14.6% | 5% | 0.4% | 64% | | 4% | 12% |
| THER 49-B | Internal layer | 0.2 mm | 73% | 25% | 2% | | | | |
| | External layer | 0.8 mm | | | | | SMA PRO20783 100% | | |
| | Total | 1 mm | 14.6% | 5% | 0.4% | 64% | | 4% | 12% |
| THER 49-C | Internal layer | 0.2 mm | 73% | 25% | 2% | | | | |
| | External layer | 0.8 mm | | | | | Ricobond 1756 100% | | |
| | Total | 1 mm | 14.6% | 5% | 0.4% | 64% | | 4% | 12% |
| THER 49-D | Internal layer | 0.2 mm | 73% | 25% | 2% | | | | |
| | External layer | 0.8 mm | | | | | Ceramer 1608 100% | | |
| | Total | 1 mm | 14.6% | 5% | 0.4% | 64% | | 4% | 12% |
| THER 49-E | Internal layer | 0.2 mm | 73% | 25% | 2% | | | | |
| | External layer | 0.8 mm | | | | | X10065 100% | | |
| | Total | 1 mm | 14.6% | 5% | 0.4% | 64% | | 4% | 12% |
| THER 49-F | Internal layer | 0.2 mm | 73% | 25% | 2% | | | | |
| | External layer | 0.8 mm | | | | | XIRAN XZ 09 004 100% | | |
| | Total | 1 mm | 14.6% | 5% | 0.4% | 64% | | 4% | 12% |
| THER 49-G | Internal layer | 0.2 mm | 73% | 25% | 2% | | | | |
| | External layer | 0.8 mm | | | | | XIRAN XZ 09 002 100% | | |
| | Total | 1 mm | 14.6% | 5% | 0.4% | 64% | | 4% | 12% |

A reference is also prepared, called THER42-F, which corresponds to a formulation with is the same as one of the formulations above, except that the compound does not comprise any coupling agent.

An analysis was then performed to evaluate if the coupling agent reacts and creates chemical bonds between fibers and polystyrene (PS), and if it is linked with mechanical cup behavior.

The results are as follows:

THER47-F (Control):

Samples present some cavities (following extrusion direction). Fibers do not present homogenous dispersion in PS, which provoke delamination. Fibers are bare, there is no chemical bond at interface between fibers and PS.

=> Bad Interfacial Cohesion

THER49-B (SMA from Cray Valley):

Fibers are well coated by PS. Cups wall thickness is regular. 2 different layers are easy to identify, and are well bonded. No delamination appears. Some micro cavities appear, which could come from thermoforming.

=> Good Coupling Between Fibers and PS and Between Two Layers.

THER49-C (PBuMA from Cray Valley):

Fibers are coated by PS but less homogenously than THER49-B. Some local delamination between fiber and PS. Fibers are concentrated in middle of layer. Some micro cavities appear, that can be due to thermoforming.

=> Coupling Between Fibers and PS and Between Two Layers, but Some Delamination.

THER49-F (SMA from Polyscope):

Cavities are present in extrusion direction, fibers are not coated by PS. Sample presents important delamination and has the same morphology as THER42-F.

=> Bad Interfacial Cohesion

As a conclusion, these analyses clearly establish if a given coupling agent acts to reinforce interface between PS and fibers.

Here, the coupling agent from Polyscope (i.e. with less than 20% by weight of the copolymer of maleic anhydride) does not create interfacial cohesion. This could be due to a lower amount of maleic anhydride compared to Cray Valley samples (8% compared to 25%).

Observations

The sheets containing SMA are particularly brittle, and are not be acceptable for the consumer feeling.

The cup weights and top loads are measured following the same protocols as for formulation 1.

Figure 2:
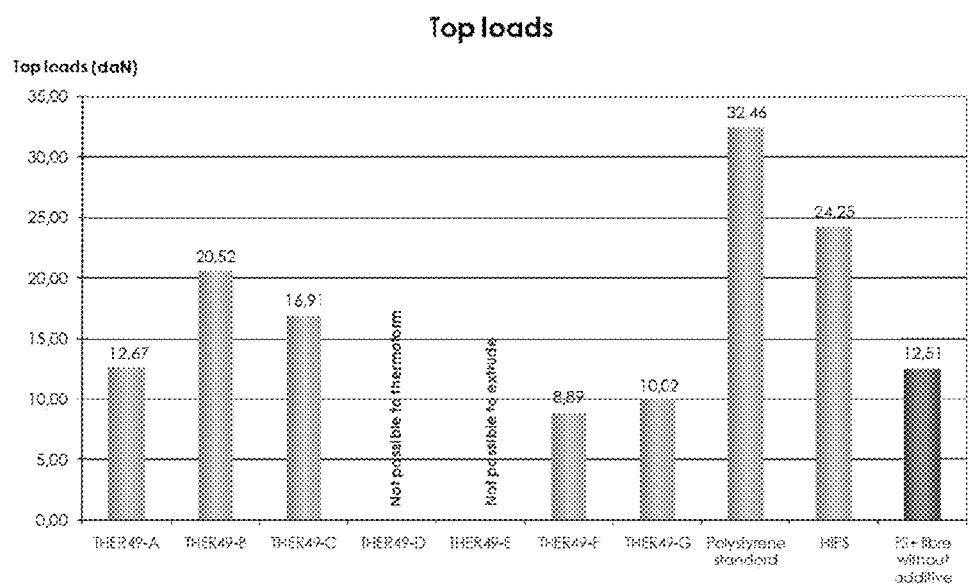
FIG. 2: Top loads measured in Example 2, following the same protocols as for formulation 1.

The results are FIGS. 1 and 2:

A weight variation between different formulas is noticed (FIG. 1). The use of coupling agent ("additive" in the figures) seems to increase cups weight. This could be explained by the presence of cavities generated during thermoforming when there is no coupling agent. Indeed, cavities will decrease cup weight by introducing air in material.

There is a huge variation of performance depending on the coupling agent (FIG. 2). The two best coupling agents are THER49-B (SMA) and THER49-C (PBuMA).

The other SMA coming from Polyscope (THER49-F) seems to contain not enough maleic anhydride to be efficient for the required application (8 and 15% versus 25% for Cray Valley).

PPMA and PEMA (THER49-D and E) do not present chemical affinity with PS matrix, so the presence of maleic anhydride at end of the backbone is not sufficient to compensate the lack of affinity.

In term of top load, SMA gives better results than PBuMA.

Conclusions:

By using the right coupling agents, cup mechanical performances can be increased.

The use of a compatibility agent (copolymer) having at least 20% by weight of the copolymer of maleic anhydride allows to increase mechanical performances.

But using SMA alone can not be acceptable as it gives very brittle cups, even if top load is higher.

Example 3

Formulations with Different Compatibility Agents (Polybutadiene Copolymers Versus Polystyrene Copolymers)

The following compatibility agents were tested: 131MA5 and 184MA6 from Ricon.

131MA5 has a lower molecular weight and a lower maleic anhydride content than 184MA6, but has a higher content of Polybutadiene versus styrene.

The following formulations were prepared:

|  | HIPS | GPPS | Cellulose Fibres 50 μm | MM 20% 131MA5* | MM 20% 184MA6* | MM 20% SMA PRO20783* | MM 20% Ricobond 1756* |
| --- | --- | --- | --- | --- | --- | --- | --- |
| Formula 1 | 38.8% | 38.8% | 15% | 7.5% | X | X | X |
| Formula 2 | 38.5% | 38.5% | 15% | X | 7.5% | X | X |
| Formula 3 | 31% | 46.50% | 15% | X | X | 3.75% | 3.75% |
| Formula 4 | 28% | 52% | 15% | X | X | 3.50% | 1.50% |
| Formula 5 | 40% | 40% | 15% | X | X | 3% | 2% |

*MM = masterbatch comprising 20% of the mentioned commercial reference (i.e. Ricon 131MA5 or 184MA6 or SMA PRO20783 or Ricobond 1756)

The sheet production formula is composed with 0.8 mm of a formulation above and 0.2 mm of pure PS for internal part.

|  |  | HIPS 6540 | GPPS 1540 | Fibres | 131MA5 | 184MA6 | SMA PRO20783 | Ricon 1756 | MM white |
|---|---|---|---|---|---|---|---|---|---|
| THER59-A | layer 0.2 mm | 58.8% | 39.2% | X | X | X | X | X | 2.0% |
|  | layer 0.8 mm | 44.75% | 38.75% | 15% | 1.5% | X | X | X | X |
|  | Total | 47.6% | 38.8% | 12% | 1.2% | X | X | X | 0.4% |
| THER59-B | layer 0.2 mm | 58.8% | 39.2% | X | X | X | X | X | 2.0% |
|  | layer 0.8 mm | 44.8% | 38.8% | 15% | X | 1.5% | X | X | X |
|  | Total | 47.6% | 38.8% | 12% | X | 1.2% | X | X | 0.4% |
| THER59-C | layer 0.2 mm | 58.8% | 39.2% | X | X | X | X | X | 2.0% |
|  | layer 0.8 mm | 37% | 46.50% | 15% | X | X | 0.75% | 0.75% | X |
|  | Total | 41.4% | 45.0% | 12% | X | X | 0.6% | 0.6% | 0.4% |
| THER59-D | layer 0.2 mm | 58.8% | 39.2% | X | X | X | X | X | 2.0% |
|  | layer 0.8 mm | 32% | 52% | 15% | X | X | 0.70% | 0.30% | X |
|  | Total | 37.4% | 49.4% | 12% | X | X | 0.6% | 0.2% | 0.4% |
| THER59-E | layer 0.2 mm | 58.8% | 39.2% |  |  |  |  |  | 2.0% |
|  | layer 0.8 mm | 44% | 40% | 15% | X | X | 0.6% | 0.40% |  |
|  | Total | 47.0% | 39.8% | 12% | X | X | 0.5% | 0.3% | 0.4% |

The cup weights and top loads were measured according to the protocols of formulation 1. Cups from experience plan present higher weight than compact PS, meaning that density without cavity could be slightly higher than PS.

Cups according to the invention were not perfectly thermoformed as the reel was too small and sheet thickness was not perfectly accurate.

Anyway cups according to the invention have a top load close to our goal.

Formulations THER 59-8 and THER 59-11 have the closest top load of the goal, but the other formulations also show good top load.

The top load of each formulation according to the invention is at least around 2 times higher than the comparative formulation without compatibility agent.

The invention claimed is:

1. A composition comprising:
   a) polystyrene, said polystyrene comprising polybutadiene;
   b) vegetal fibers having a length lower than 50 μm; and
   c) at least one compatibility agent comprising a polybutadiene maleic anhydride copolymer, said copolymer comprising at least 17% by weight of the copolymer of maleic anhydride.

2. The composition according to claim 1, wherein said polystyrene a) is selected from the group consisting of High Impact PolyStyrene, and mixtures of High Impact PolyStyrene and General Purpose PolyStyrene.

3. The composition according to claim 1, wherein said vegetal fibers b) are selected from the group consisting of cellulose fibers, flax fibers, hemp fibers, cotton fibers, jute fibers, ramie fibers, sisal fibers, algae fibers and their mixtures.

4. The composition according to claim 1, wherein said vegetal fibers b) are present in an amount of 1% to 30% by weight of the total weight of the composition.

5. The composition according to claim 1, where said compatibility agent c) is chosen from:
   polybutadiene maleic anhydride copolymers comprising at least 17% by weight of the copolymer of maleic anhydride, and
   mixtures of polybutadiene maleic anhydride copolymers comprising at least 17% by weight of the copolymer of maleic anhydride, and styrene maleic anhydride copolymers.

6. The composition according to claim 1, wherein said compatibility agent c) is present in an amount of 0.1 to 3% by weight of the total weight of the composition.

7. The composition according to claim 1, wherein said compatibility agent c) comprises at most 30% by weight of the copolymer of polybutadiene.

8. The composition according to claim 1, wherein said polystyrene a) is a mixture of High Impact PolyStyrene and General Purpose PolyStyrene, in a weight ratio of 30:70 to 60:40.

9. The composition according to claim 1 in the form of a plastic composition, obtained by a step of heating the mixture of ingredients a), b) and c).

10. The composition according to claim 1, wherein the composition is in a form of powder, granules or pellets.

11. The composition according to claim 1, wherein the composition is in a form of a sheet or film, obtained by extrusion.

12. The composition according to claim 11, wherein the composition is in a form of a container, obtained by thermoforming the sheet.

13. A process of manufacturing a product of a desired shape, comprising:
   i) mixing and heating the following ingredients, so as to obtain a plastic composition:
      a) polystyrene, said polystyrene comprising polybutadiene;
      b) vegetal fibers having a length lower than 50 μm; and
      c) at least one compatibility agent comprising a polybutadiene maleic anhydride copolymer, said copolymer comprising at least 17% by weight of the copolymer of maleic anhydride,
   ii) extruding the plastic composition obtained in step i), so as to obtain a sheet or a film, and
   iii) thermoforming the sheet or film obtained in step ii).

14. The process according to claim 13, wherein the product is a yogurt container.

15. The composition according to claim 1, wherein said vegetal fibers b) are present in an amount of 5% to 20% by weight of the total weight of the composition.

16. The composition according to claim 1, wherein said compatibility agent c) is present in an amount of 1 to 1.5% by weight of the total weight of the composition.

* * * * *